United States Patent
Towell et al.

(10) Patent No.: US 10,407,586 B2
(45) Date of Patent: Sep. 10, 2019

(54) SEED COATING COMPOSITIONS INCLUDING ETHYLENE COPOLYMER AND LUBRICANT

(71) Applicant: Michelman, Inc., Cincinnati, OH (US)

(72) Inventors: David B. Towell, Cincinnati, OH (US); Jim Stephens, Cincinnati, OH (US)

(73) Assignee: Michelman, Inc., Cincinnati, OH (US)

( * ) Notice: Subject to any disclaimer, the term of this patent is extended or adjusted under 35 U.S.C. 154(b) by 0 days.

(21) Appl. No.: 15/656,573

(22) Filed: Jul. 21, 2017

(65) Prior Publication Data
US 2018/0030306 A1    Feb. 1, 2018

Related U.S. Application Data

(60) Provisional application No. 62/367,916, filed on Jul. 28, 2016.

(51) Int. Cl.
| | |
|---|---|
| *A01N 25/10* | (2006.01) |
| *C09D 123/08* | (2006.01) |
| *A01C 1/06* | (2006.01) |
| *C09D 5/00* | (2006.01) |
| *C09D 191/06* | (2006.01) |
| *A01N 25/26* | (2006.01) |

(52) U.S. Cl.
CPC .......... *C09D 123/0876* (2013.01); *A01C 1/06* (2013.01); *A01N 25/10* (2013.01); *A01N 25/26* (2013.01); *C09D 5/00* (2013.01); *C09D 191/06* (2013.01)

(58) Field of Classification Search
CPC .......... A01N 25/00; A01N 25/30; C09D 5/00; C09D 123/0876; A01C 1/06
See application file for complete search history.

(56) References Cited

U.S. PATENT DOCUMENTS

| | | | | |
|---|---|---|---|---|
| 3,867,324 A * | 2/1975 | Clendinning | .......... | A01C 1/046 523/126 |
| 3,905,152 A * | 9/1975 | Loperfido | ................ | A01C 1/06 47/57.6 |
| 2002/0134012 A1* | 9/2002 | Ding | ........................ | A01C 1/06 47/57.6 |
| 2007/0207927 A1* | 9/2007 | Rosa | ........................ | A01C 1/06 504/100 |
| 2014/0274682 A1 | 9/2014 | Wu et al. | | |
| 2017/0127670 A1 | 5/2017 | Bueno et al. | | |

FOREIGN PATENT DOCUMENTS

| | | |
|---|---|---|
| EP | 0 289 827 A2 | 11/1988 |
| WO | 2010086303 A2 | 8/2010 |
| WO | 2013158284 A1 | 10/2013 |
| WO | 2013166012 A1 | 11/2013 |
| WO | 2013166020 A1 | 11/2013 |
| WO | 2016055439 A1 | 4/2016 |

OTHER PUBLICATIONS

International Search Report and Written Opinion dated Jun. 10, 2017 pertaining to International Application No. PCT/US2017/043625.

* cited by examiner

*Primary Examiner* — Johann R Richter
*Assistant Examiner* — Danielle Sullivan
(74) *Attorney, Agent, or Firm* — Vorys, Sater, Seymour and Pease LLP

(57) ABSTRACT

Coated seeds and methods for reducing seed dust and increasing seed flowability are disclosed. The coated seeds include a seed and a coating composition. The coating composition includes a binder comprising an ethylene copolymer and a lubricant comprising a wax composition. In some embodiments, the ethylene copolymer includes an ethylene monomer and at least one comonomer. The comonomer is selected from acrylic acid, acetic acid, derivatives thereof, or mixtures thereof. In some embodiments, the wax comprises a Fischer-Tropsch wax, a carnauba wax, a polyethylene wax, a soy wax, a paraffin wax, a scale wax, a slack wax, or a mixture thereof.

16 Claims, 1 Drawing Sheet

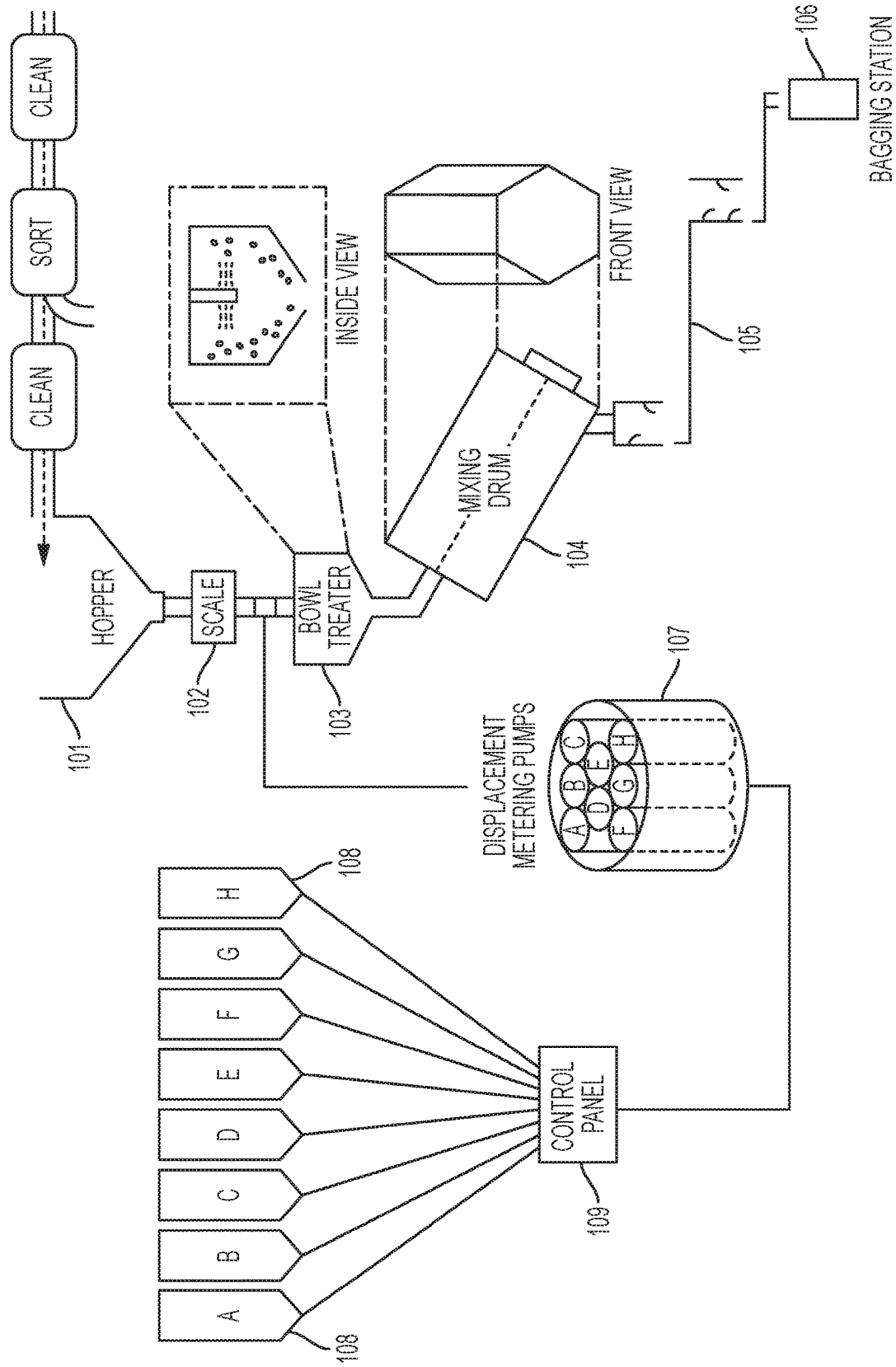

SEED COATING COMPOSITIONS INCLUDING ETHYLENE COPOLYMER AND LUBRICANT

CROSS-REFERENCE TO RELATED APPLICATIONS

This application claims priority to U.S. Provisional Patent Application Ser. No. 62/367,916 filed Jul. 28, 2016, and entitled "Seed Coating Compositions Including Ethylene Copolymer and Lubricant," the entirety of which is incorporated by reference herein.

TECHNICAL BACKGROUND

The present specification relates generally to coating compositions. More specifically, the present specification relates to seed coating compositions including ethylene copolymers and a lubricant.

BACKGROUND

Two problems associated with the sowing of seeds using seed sowing equipment include dust drift and flowability. Dust drift or dust-off relates to the loss of particles of the seed coat and loose particulate material including the untargeted spread of pesticides when the seeds are handled. Generation of dust can adversely affect the environment. Flowability relates to the ability of seeds to slide through the equipment, such as a planter. Low flowability can lead to clumping of seeds, plugging of the planter, inconsistent flow through the planter, and uneven planting of a crop. Accordingly, there is a need to provide seeds having improved flowability and decreased dust.

SUMMARY

According to one or more embodiments, a coated seed includes a seed and a coating. The coating includes a binder and, optionally, a lubricant and may be used in conjunction with a seed treatment pesticide. The binder includes an ethylene copolymer that includes greater than 50% by weight of an ethylene monomer and at least one comonomer. The at least one comonomer includes one or more components selected from acrylic acid, acetic acid, derivatives thereof, or mixtures thereof.

According to one or more embodiments, a coated seed includes a seed and a coating. The coating includes a binder and a lubricant and may be used in conjunction with a seed treatment pesticide. The binder includes an ethylene copolymer that includes an ethylene monomer and at least one comonomer. The at least one comonomer includes one or more components selected from acrylic acid, acetic acid, derivatives thereof, or mixtures thereof.

According to one or more embodiments, a coated seed includes a seed and a coating. The coating includes a binder and a lubricant and may be used in conjunction with a seed treatment pesticide. The binder includes an ethylene copolymer that includes greater than 40% by weight of an ethylene monomer and at least one comonomer.

According to one or more embodiments, a method of reducing seed dust and increasing seed flowability includes treating a seed with a coating composition. The coating composition includes an ethylene copolymer and at least one wax. The ethylene copolymer includes greater than 40% by weight of an ethylene monomer and at least one comonomer. The at least one comonomer includes one or more components selected from acrylic acid, acetic acid, derivatives thereof, or mixtures thereof.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 1 is a schematic depiction of an embodiment of the seed coating process.

The embodiments set forth in the drawing are illustrative in nature and not intended to be limiting to the claims. Moreover, individual features of the drawing will be more fully apparent and understood in view of the detailed description.

DETAILED DESCRIPTION

Various embodiments include coated seed that includes a seed and a coating. The coating includes an ethylene copolymer and a lubricant that, when applied to the seed, enhances flowability of the seed. As used herein, "copolymer" encompasses polymers produced from at least two monomers and could include polymers having more than two comonomers such as terpolymers, tetrapolymers, etc.

In various embodiments, the ethylene copolymer includes an ethylene monomer and at least one comonomer. The comonomer includes one or more components selected from acrylic acid, acetic acid, derivatives thereof, or mixtures thereof. The lubricant may be a wax. The wax can be, for example, an animal, plant, mineral, or petroleum wax. Example waxes may include, by way of example and not limitations, an emulsion or micronized wax including a Fischer-Tropsch wax, a carnauba wax, a polyethylene wax, a soy wax, a paraffin wax, a scale wax, a slack wax, other vegetable waxes, or mixtures thereof.

In one embodiment, the ethylene copolymer is in the form of a polymer dispersion. In one or more specific embodiments, the dispersion is a water-based polymer dispersion, for example, a colloidal water-based dispersion. In one embodiment, the colloidal dispersion may be an ionomer prepared by heating the solid ethylene copolymer with a water phase in a pressure reactor in the presence of a base (for example, ammonia) such that the base reacts with the acid groups on the polymer, and upon melting, the colloidal dispersion is formed. Other methods for making the polymer dispersion are contemplated herein. In one or more embodiments, the polymer dispersion may contain about 10 to 50% by weight of ethylene copolymer solids, from about 25 to 50% by weight of ethylene copolymer solids, or from about 30 to 45% of ethylene copolymer solids.

The coating may be applied to a seed with a coating weight of from about 50 to about 200 mL per 45.4 kg of seed. Depending on the seed, the coating may have a thickness of from about 0.5 microns to about 5.0 microns. The seeds can be any type of seed, including, for example, cereals, vegetables, ornamentals, and fruits. In particular, the seeds may be, by way of example and not limitation, soybean seeds, corn seeds, cotton seeds, rice seeds, oat seeds, rye seeds, barley seeds, vegetable seeds, wheat seeds, sunflower seeds, lettuce seeds, spinach seeds, or the like.

The coating can be performed, for example, using a batch coater, a drum coater, or the like. In some embodiments, the coating method employed may depend on the particular type of seed to be coated. An exemplary drum coater 100 for use in various embodiments is illustrated in FIG. 1. As shown in FIG. 1, seeds are cleaned, sorted, and added to a supply hopper 101. The seeds flow through the supply hopper 101 to a scale 102 and into a bowl treater 103. In various embodiments, the supply hopper 101 and the scale 102 control the rate of seed flow into the bowl treater 103. In the bowl treater 103, the seeds pass through a zone of sprayed or atomized coating material, where the seeds come into contact with the components of the seed coating. The seeds pass from the bowl treater 103 into a mixing drum 104.

The mixing drum 104 rotates the seeds and the seed coating, agitating the seeds and ensuring that each seed is substantially completely coated with the seed coating. The coated seeds then exit through an opening of the mixing drum 104. Coated seeds exiting the mixing drum 104 may contact one or more conveyor belts 105 which transport the seeds to a bagging station 106.

In various embodiments, the drum coater 100 includes one or more metering pumps 107 that provide the coating to the bowl treater 103. In particular, the metering pump 107 draws the coating composition or coating components from one or more tanks 108 as directed by the control panel 109.

Although various embodiments described herein employ spraying the coating onto the seeds, it should be understood that the seed may be coated with the coating according to any suitable coating process. As but one example, the seeds may be mixed with the coating. In other embodiments, the seed may be tumbled with the coating composition, film coated, pelleted, encrusted, or the like.

In various embodiments, the seed coating is a mixture including at least the ethylene copolymer and the lubricant. In some embodiments, the seed coating may include additional components, such as one or more pesticides, one or more fungicides, one or more surfactants, shellac, one or more colorants, one or more fertilizers, one or more nutrients, one or more moisture modifiers, and the like. It should be understood that the particular components included in the mixture can vary depending on the particular embodiment.

In other embodiments, such as the embodiment depicted in FIG. 1, the seed coating is a plurality of independent components with which the seed is coated simultaneously or substantially simultaneously. For example, instead of coating the seed with a mixture that includes all of the components, one or more components of the seed coating can be applied to the seed individually or as part of a different mixture during the seed coating process. In other words, the components that make up the seed coating can be drawn from one or more tanks 108. Therefore, in various embodiments, the lubricant, the polymer dispersion, and any additional components in the seed coating can be coated on the seed simultaneously or substantially simultaneously independent of whether or not they are mixed together prior to coating.

In one or more embodiments, the ethylene copolymer may include greater than 40% by weight or greater than 50% by weight of an ethylene monomer. In some embodiments, the ethylene copolymer includes from about 60% to about 98% by weight ethylene monomer. In other embodiments, the ethylene copolymer includes from about 70% to about 90% by weight ethylene monomer.

Moreover, the ethylene copolymer may include up to about 60 by weight or up to about 50% by weight of the at least one comonomer. In some embodiments, the ethylene copolymer includes from about 2% to about 40% by weight comonomer. In other embodiments, the ethylene copolymer includes from about 10% to about 30% by weight comonomer. In various embodiments, the comonomer includes one or more components selected from acrylic acid, acetic acid, derivatives thereof, or mixtures thereof. In some embodiments, the comonomer includes an acrylic acid comonomer. The acrylic acid comonomer may include, by way of example and not limitation, acrylic acid, acrylic acid derivatives, or combinations thereof. As used herein, "derivatives" means that the monomer has at least additional moiety or group substituted to the monomer. For example, one acrylic acid comonomer derivative may be methacrylic acid, which is acrylic acid modified with an additional methyl group. A suitable ethylene acrylic acid dispersion for use in the present disclosure is commercially available from Michelman under the designation Michem® Prime 4983.

In other embodiments, the comonomer includes an acetic acid comonomer. The acetic acid comonomer may include, by way of example and not limitation, acetic acid, acetic acid derivatives, or combinations thereof. In some embodiments, the acetic acid comonomer may be a vinyl acetate comonomer.

According to various embodiments, the ethylene copolymer is formed by high pressure polymerization. For example, the ethylene copolymer may be formed at a pressure from about 2,500 psi to about 50,000 psi.

The lubricant can be, for example, a wax. The wax may be a micronized wax or wax emulsion including a Fischer-Tropsch wax, a carnauba wax, a polyethylene wax, a soy wax, a paraffin wax, a scale wax, a slack wax, a micronized wax, or mixtures thereof. The emulsions may be emulsions comprising one or more solvents as well as additional components. For example, these solvents may include one or more of water, surfactants, preservatives, acids, or bases. The wax emulsion may include between about 40% and about 90% water by weight. Various surfactants are contemplated, for example, non-ionic surfactants, and anionic surfactants. In one embodiment, the non-ionic surfactant may include ethoxylated alcohols. These ethoxylated alcohols may include ethoxylated fatty alcohols, wherein fatty alcohols are long chain alcohols having from 4 to 50 carbons. Moreover, the anionic surfactants may include anionic sulfonated surfactants and fatty acid salts. The wax emulsion may include between about 0.5% and about 12% surfactant by weight. Furthermore, various preservatives are contemplated for the wax emulsions, for example, glutaraldehyde and benzisothiazolinone. In embodiments that include preservatives, the wax emulsion may include between 0% and 0.5% preservative by weight.

The wax emulsion may include between about 5% and about 60% wax by weight, or between about 10% and about 45% wax by weight. In some embodiments, the wax emulsion includes between about 5% and about 60%, between about 10% and about 15%, between about 21% and about 24%, or between about 33% and about 45% of the wax by weight. According to some embodiments, the emulsion may be nonionic or anionic. The wax emulsion may have a pH of between 3.0 and about 10.0. In some embodiments, the wax emulsion has a pH of between about 5.0 and about 8.0 or between about 4.0 and about 7.0. The wax emulsion can be, for example, commercially available wax emulsions such as NurtureYield® S2101, NurtureYield® S2103, or NurtureYield® S2001 from Michelman, Inc. (Cincinnati, Ohio).

In various embodiments, the polymer dispersion and the lubricant are combined to form a coating composition prior to application to the seeds. The polymer dispersion and the lubricant may be combined such that the coating composition includes between about 10% and about 70% of the polymer dispersion by volume. In embodiments in which the various components of the seed coating are applied substantially simultaneously to the seed, the polymer dispersion may be applied at a ratio by volume of between about 1:10 and about 10:1 of polymer dispersion to lubricant. In a further embodiment, the ratio by volume of polymer dispersion to lubricant is about 1:1 to about 3:1. In some embodiments, the coating composition includes about 50% of the polymer dispersion and about 50% of the lubricant by weight.

It should now be understood that various aspects of the seed coating compositions and methods for coating seeds are described herein and that such aspects may be utilized in conjunction with various other aspects.

EXAMPLES

The following non-limiting examples illustrate various seed coating compositions and various properties associated therewith.

Methods of Making Sample Formulations

Example 1

Michem® Prime 4983R, a polymer dispersion including ethylene acrylic acid copolymer neutralized ammonia available from Michelman Inc. (Cincinnati, Ohio), was mixed with NurtureYield® S2101 in a ratio of approximately 1:1 to form a seed coating composition. NurtureYield® S2101 is a wax emulsion including Fischer-Tropsch wax in a high molecular weight alcohol ethoxylate, benzisothiazolinone, and water available from Michelman Inc. (Cincinnati, Ohio).

Example 2

Michem® Prime 4983R was mixed with NurtureYield® S2001 in a ratio of approximately 1:1 to form a seed coating composition. NurtureYield® S2001 is a wax emulsion including carnauba wax in ammonium lauryl sulfate, a preservative, and water available from Michelman Inc. (Cincinnati, Ohio).

Example 3

Michem® Prime 4825R was mixed with NurtureYield® S2101 in a ratio of approximately 1:1 to form a seed coating composition. Michem® Prime 4825R is a polymer dispersion including ethylene acrylic acid copolymer neutralized with sodium hydroxide available from Michelman Inc. (Cincinnati, Ohio).

Example 4

Michem® Prime 4825R was mixed with NurtureYield® S2001 in a ratio of approximately 1:1 to form a seed coating composition.

Example 5

Michem® Prime 4983R was mixed with NurtureYield® S2104 in a ratio of approximately 1:1 to form a seed coating composition. NurtureYield® S2104 is a wax emulsion including Fischer-Tropsch wax in a mixture of ethoxylated fatty alcohol surfactants, glutaraldehyde, 90% potassium hydroxide, oxidized polyethylene, and water available from Michelman Inc. (Cincinnati, Ohio).

Adhesion and Flow Testing Examples

The following examples of Table 1 are tested for their coating adhesion and seed flow properties according to the procedures described below.

TABLE 1

| Example | Ethylene Copolymer | Wax | Volume Ratio of Polymer Dispersion (Binder) to Wax Emulsion (Lubricant) |
|---|---|---|---|
| Example 6 | Michem ® Prime 4983R Ethylene Acrylic Acid (20% acrylic acid) from Michelman Inc. | None | N/A |
| Example 7 | Michem ® Prime 4983R | NurtureYield ® S2001 carnauba wax emulsion from Michelman Inc. | 50/50 |
| Example 8 | Michem ® Prime 4983R | NurtureYield ® S2101 Fischer-Tropsch wax emulsion from Michelman Inc. | 70/30 |
| Example 9 | Michem ® Prime 4983R | NurtureYield ® S2101 | 50/50 |
| Example 10 | 161127CX Ethylene Methacrylic Acid from Michelman Inc. | None | N/A |
| Example 11 | Wax Modified 161127CX | NurtureYield ® S2101 from Michelman Inc. | 50/50 |
| Example 12 | 161128CX Ionomer of Ethylene Methacrylic Acid Copolymer from Michelman Inc. | None | N/A |
| Example 13 | Wax Modified 161128CX Ethylene | Ionomer of EthyleneMethacrylic Acid | 50/50 |

TABLE 1-continued

| Example | Ethylene Copolymer | Wax | Volume Ratio of Polymer Dispersion (Binder) to Wax Emulsion (Lubricant) |
|---|---|---|---|
| | Methacrylic Acid from Michelman Inc. | Copolymer/NurtureYield ® S2101 Fischer Tropsch Wax Emulsion | |
| Example 14 | Michem ® Emulsion 44730 Ethylene Acrylic Acid Copolymer (5% acrylic acid) from Michelman Inc. | None | N/A |

Seeds were coated and dried at ambient conditions for approximately 24 hours on paperboard. To test for coating adhesion, 50 g mass samples of coated soybean seeds, which were individually coated with the Examples of Table 1, were poured into jars. Then, the jars were placed in a Red Devil Shaker (which is analogous to a paint shaker) so that the coated seeds were shaken on speed #2 for 60 seconds.

Post-shaking, the mass of the seeds were then weighed again with an analytical balance with effort made to exclude the dust and loose particles from the final seed mass.

From these seed mass values, the percent (%) dust-off was calculated. The % dust-off was measured by the following equation:

% dust-off=$(m_1-m_2)/m_1 \times 100\%$ wherein $m_1$ is the seed sample weight pre-shaking, and $m_2$ is the seed sample weight post-shaking. A lower percent (%) dust-off indicates lower mass loss of the seed after during shaking.

To test for how well the seeds flow or slide past each other, coated seeds were passed through a funnel. They were timed on how quickly they passed through or how many times they stopped moving and needed to be agitated. Additionally, the time for the seeds to complete flow through was measured. To agitate the seeds, the bottom of the funnel was tapped with a finger one tap at a time till at least 1 seed fell. The seeds were added rapidly so that few of them could pass through the funnel unimpeded by other seeds.

In this test, 125 grams of coated soybean seeds for each of the Example coatings of Table 2 are each passed through a flow funnel. The funnel had a diameter of 10.795 cm at the mouth and 1.75 cm at the spout and a length of 10.975 cm. The diameter of the coated soybean seed was roughly 6.74 millimeters. Five replications of the flow test, which are denoted as $t_1$–$t_5$ below in Table 2, were measured and averaged. As shown in Table 2 below, Examples 6, 10, 12, and 14, which include ethylene copolymers and no wax, did not possess sufficient lubricity as indicated by the "stick" notation. "Stick" means that the seeds would not fully flow unless it was tapped and agitated with a finger. In contrast, the wax containing coatings possessed sufficient lubricity and flowed through the tunnel without intervention (i.e., sticks).

TABLE 2

| Example | T1 (secs) | T2 (secs) | T3 (secs) | T4 (secs) | T5 (secs) | Avg (secs) | Flow score | Dust wt (gms) | % Dust-off | Dust-off score |
|---|---|---|---|---|---|---|---|---|---|---|
| Example 6 | 3.34 | 1 stick | 1 stick | 3.75 | 3.3 | | 8 | 0.0016 | 0.00319% | 10 |
| Example 7 | 3.07 | 2.84 | 2.98 | 3.02 | 2.91 | 2.964 | 10 | 0.0034 | 0.0068% | 8 |
| Example 8 | 3.06 | 3.07 | 3.06 | 3.02 | 3.07 | 3.056 | 10 | 0.0061 | 0.0122% | 6 |
| Example 9 | 2.91 | 2.79 | 2.93 | 2.87 | 2.83 | 2.866 | 10 | −0.0027 | 0.0060% | 9 |
| Example 10 | 3.8 | 4.04 | 3.99 | 1 stick | 2 sticks | | 8 | | 0.01040% | 7 |
| Example 11 | 3.17 | 3.27 | 3.12 | 3.25 | 3.38 | 3.238 | 10 | 0.0115 | 0.02294% | 2 |
| Example 12 | 1 stick | 3.69 | 3.24 | 1 stick | 1 stick | | 7 | 0.0075 | 0.01500% | 5 |
| Example 13 | 3.63 | 3.63 | 3.45 | 3.23 | 3.13 | 3.414 | 10 | 0.0021 | 0.00420% | 10 |
| Example 14 | 1 Stick | 3 Stick | 1 stick | 1 stick | 1 stick | | 4 | 0.0055 | 0.0110% | 7 |

ADDITIONAL EXAMPLES

Various properties of the following examples of Table 3 are tested according to the procedures described below.

TABLE 3

| Example | Ethylene Copolymer | Wax | Seed Coating amount |
|---|---|---|---|
| Example 15 | Michem ® Prime 4983R Ethylene Acrylic Acid (20% acrylic acid) | None | 1 fl oz/100 lb of seed |
| Example 16 | Michem ® Prime 4983R | None | 2 fl oz/100 lb of seed |
| Example 17 | Michem ® Prime 4983R | NurtureYield ® S2101 Fischer-Tropsch Wax Emulsion | 1 fl oz/100 lb of seed |
| Example 18 | Michem ® Prime 4983R | NurtureYield ® S2101 | 2 fl oz/100 lb of seed |

For the tests described below, the seed used were corn and soybean seeds. The laboratory testing methods check for plantability, dust off, flowability (4 replications of 300 g) and germination. Referring to Table 3, the coatings were applied at the above-stated amounts. Results are provided in Table 4 below.

Coatings were applied using a Hege seed treater. Plantability was tested using 1000 seeds in a Precision Planting eSet meter. The planting meter was at a standard setting (33,000 seeds/acre for corn, and 16,000 seeds/acre for soybeans) a speed of 4.2 mph and a vacuum rate of 18.1. The vacuum planting unit simulates planting in the field and uses air pressure to attach the seeds to the disk while measuring the proper alignment, skips, multiples and misalignments. Results can be provided in many forms, but most commonly the percent singulation (the percent of 1000 seeds in which one seed is aligned to be planted in one hole) of 1000 seeds is provided.

To measure dust-off, two 100 g seed samples were run through the Heubach Dustmeter. Temperature and relative humidity were recorded and fell within range of 20° C. to 25° C. and 30% to 70% RH. A seed count was performed to determine the mean grams of dust per 100,000 seeds. The current European Standard for allowable dust is 0.75 grams per 100,000 seeds.

Four replications of 300 grams of seed were each run through a flow funnel. Drop Distance (height of funnel from pan), funnel area opening, and length of funnel tube were all recorded. The funnel was 4.5 cm from the pan. The area of the funnel bottom was 2.22 cm. The funnel tube was 14.7 cm long. The time for the seeds to complete flow through was measured.

Additionally, to measure germination, a standard warm germination test was conducted wherein each 100 seed replicate is planted on moistened crepe cellulose paper and place into 25° C. for seven days after which the seedlings are evaluated as normal, abnormal and dead according to Association of Official Seed Analysts (AOSA) rules. Germination can be defined as the emergence, sprouting and development from the seed embryo of essential structures to develop into normal plants under favorable conditions in soil.

TABLE 4

| Ex. | Corn Germ. | Soybean Germ. | Corn Dust | Soybean Dust | Corn Flow. (secs) | Soybean Flow. (secs) | Corn Sing. (%) | Soybean Sing. (%) |
| --- | --- | --- | --- | --- | --- | --- | --- | --- |
| 15 | 96 | 87 | 0.095 | 0.009 | 2.7 | 2.2 | 99.9 | 87.6 |
| 16 | 95 | 86 | 0.27 | 0.007 | 3.2 | 2.4 | 99.7 | 86.1 |
| 17 | 95 | 88 | 0.029 | 0.004 | 2.6 | 1.6 | 99.9 | 89.4 |
| 18 | 95 | 86 | 0.059 | 0.010 | 2.8 | 1.8 | 100 | 86.3 |

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

It is noted that terms like "preferably," "generally," "commonly," and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited are incorporated herein by reference; the citation of any document is not to be construed as an admission that it is prior art with respect to the present disclosure.

It is to be further understood that where descriptions of various embodiments use the term "comprising," and/or "including" those skilled in the art would understand that in some specific instances, an embodiment can be alternatively described using language "consisting essentially of" or "consisting of."

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

What is claimed is:

1. A coated seed comprising a seed and a coating, wherein the coating comprises:
    a binder comprises an ethylene copolymer, wherein the ethylene copolymer comprises an ethylene monomer in an amount of from about 70% to about 90% by weight based on the weight of the ethylene copolymer, and from about 10% to about 30% by weight of at least one comonomer selected from the group consisting of acrylic acid and methacrylic acid; and
    a lubricant.

2. The coated seed according claim 1, wherein the lubricant comprises a wax.

3. The coated seed according to claim 2, wherein the wax comprises a Fischer-Tropsch wax, a carnauba wax, a polyethylene wax, a soy wax, a paraffin wax, a scale wax, a slack wax, a micronized wax, another vegetable wax, or a mixture thereof.

4. The coated seed according to claim 1, wherein the seed is selected from soybean, corn, cotton, rice, oat, rye, barley, wheat, sunflower, lettuce, spinach, and vegetable.

5. The coated seed according to claim 1, wherein the coating further comprises at least one pesticide.

6. The coated seed according to claim 1, wherein the coating further comprises a colorant.

7. The coated seed according to claim 1, wherein the coating comprises a ratio by weight of binder to lubricant of about 1:10 to about 10:1.

8. The coated seed according to claim 7, wherein the ratio by weight of binder to lubricant of about 1:1 to about 3:1.

9. The coated seed according to claim 1, wherein the ethylene copolymer is an ionomer.

10. A method of reducing seed dust and increasing seed flowability comprising:
   treating a seed with a coating composition, wherein the coating composition comprises a lubricant and a binder comprising:
      ethylene copolymer, wherein the ethylene copolymer comprises an ethylene monomer in an amount of from about 70% to about 90% by weight based on the weight of the ethylene copolymer, and from about 10% to about 30% by weight of at least one comonomer selected from the group consisting of acrylic acid and methacrylic acid.

11. The method according to claim 10, wherein the coating comprises a ratio by weight of binder to lubricant of about 1:10 to about 10:1.

12. The method according to claim 10, wherein the coating composition further comprises at least one pesticide.

13. The method according to claim 10, wherein the ethylene copolymer is formed by high pressure polymerization at pressures of about 2,500 to about 50,000 psi.

14. The method according to claim 10, wherein treating the seed with the coating composition comprises spraying the seed with the coating composition.

15. The method according to claim 14, the method further comprising agitating the seed following spraying, the agitating being effective to coat the seed with the coating composition.

16. The method according to claim 10, wherein treating the seed with the coating composition comprises tumbling the seed with the coating composition.

* * * * *